US 8,858,451 B2

(12) United States Patent
Pfeiffer et al.

(10) Patent No.: US 8,858,451 B2
(45) Date of Patent: Oct. 14, 2014

(54) BLOOD VESSEL CATHETER AND INJECTION SYSTEM FOR CARRYING OUT A BLOOD PRESSURE MEASUREMENT OF A PATIENT

(75) Inventors: Ulrich Pfeiffer, Munich (DE); Daniel Moulas, Basel (CH); Reinhold Knoll, Neuburg a.Inn (DE)

(73) Assignee: Edwards Lifesciences IPRM AG, Nyon (CH)

( * ) Notice: Subject to any disclaimer, the term of this patent is extended or adjusted under 35 U.S.C. 154(b) by 0 days.

(21) Appl. No.: 13/489,319

(22) Filed: Jun. 5, 2012

(65) Prior Publication Data

US 2012/0330168 A1    Dec. 27, 2012

Related U.S. Application Data

(63) Continuation of application No. 11/637,546, filed on Dec. 12, 2006, now abandoned.

(30) Foreign Application Priority Data

Dec. 15, 2005  (DE) .......................... 10 2005 060 079

(51) Int. Cl.
| | |
|---|---|
| *A61B 5/02* | (2006.01) |
| *A61M 25/00* | (2006.01) |
| *A61B 5/0215* | (2006.01) |
| *A61M 5/14* | (2006.01) |
| *A61M 39/02* | (2006.01) |
| *A61M 39/22* | (2006.01) |

(52) U.S. Cl.
CPC ...... *A61B 5/0215* (2013.01); *A61M 2205/3344* (2013.01); *A61M 25/0097* (2013.01); *A61M 2039/0205* (2013.01); *A61M 5/14* (2013.01); *A61M 39/22* (2013.01); *A61M 2005/1403* (2013.01)
USPC .......................................... 600/486; 600/485

(58) Field of Classification Search
USPC .................................................. 600/485–499
See application file for complete search history.

(56) References Cited

U.S. PATENT DOCUMENTS

| | | | |
|---|---|---|---|
| 2,615,463 | A | 10/1952 | Burns |
| 3,581,734 | A | 6/1971 | Croslin et al. |
| 3,662,743 | A | 5/1972 | Amarante et al. |
| 3,834,372 | A | 9/1974 | Turney |
| 3,996,926 | A * | 12/1976 | Birnbaum ...................... 600/486 |
| 4,160,448 | A | 7/1979 | Jackson |
| 4,431,009 | A | 2/1984 | Marino, Jr. et al. |
| 4,444,198 | A | 4/1984 | Petre |
| 4,545,389 | A | 10/1985 | Schaberg et al. |

(Continued)

FOREIGN PATENT DOCUMENTS

| | | |
|---|---|---|
| EP | 0 276 535 A1 | 8/1988 |
| EP | 1 776921 A2 | 4/2007 |
| WO | WO-2005/086753 A2 | 9/2005 |

*Primary Examiner* — Michael Kahelin
*Assistant Examiner* — Karen Toth
(74) *Attorney, Agent, or Firm* — Michael Crapenhoft

(57) ABSTRACT

An injection system for injecting an injectate fluid into a blood vessel of the patient and for carrying out a blood pressure measurement of a patient. The injection system includes a catheter tube having a first end for penetrating the blood vessel of the patient, and a pressure sensor which is arranged close to a second end of the catheter tube and can sense a pressure of a liquid in the catheter tube as an indication of the blood pressure of the patient.

2 Claims, 14 Drawing Sheets

(56) References Cited

U.S. PATENT DOCUMENTS

| | | |
|---|---|---|
| 4,576,180 A | 3/1986 | Taheri |
| 4,819,653 A * | 4/1989 | Marks .................. 600/486 |
| 5,002,066 A | 3/1991 | Simpson et al. |
| 5,128,519 A | 7/1992 | Tokuda |
| 5,148,811 A | 9/1992 | Messinger |
| 5,168,901 A | 12/1992 | Marks |
| 6,021,797 A * | 2/2000 | Gaines ........................ 137/2 |
| 6,128,519 A | 10/2000 | Say |
| 6,669,051 B1 | 12/2003 | Phallen et al. |
| 6,918,893 B2 * | 7/2005 | Houde et al. .................. 604/248 |
| 2006/0000448 A1 | 1/2006 | Ricco et al. |

* cited by examiner

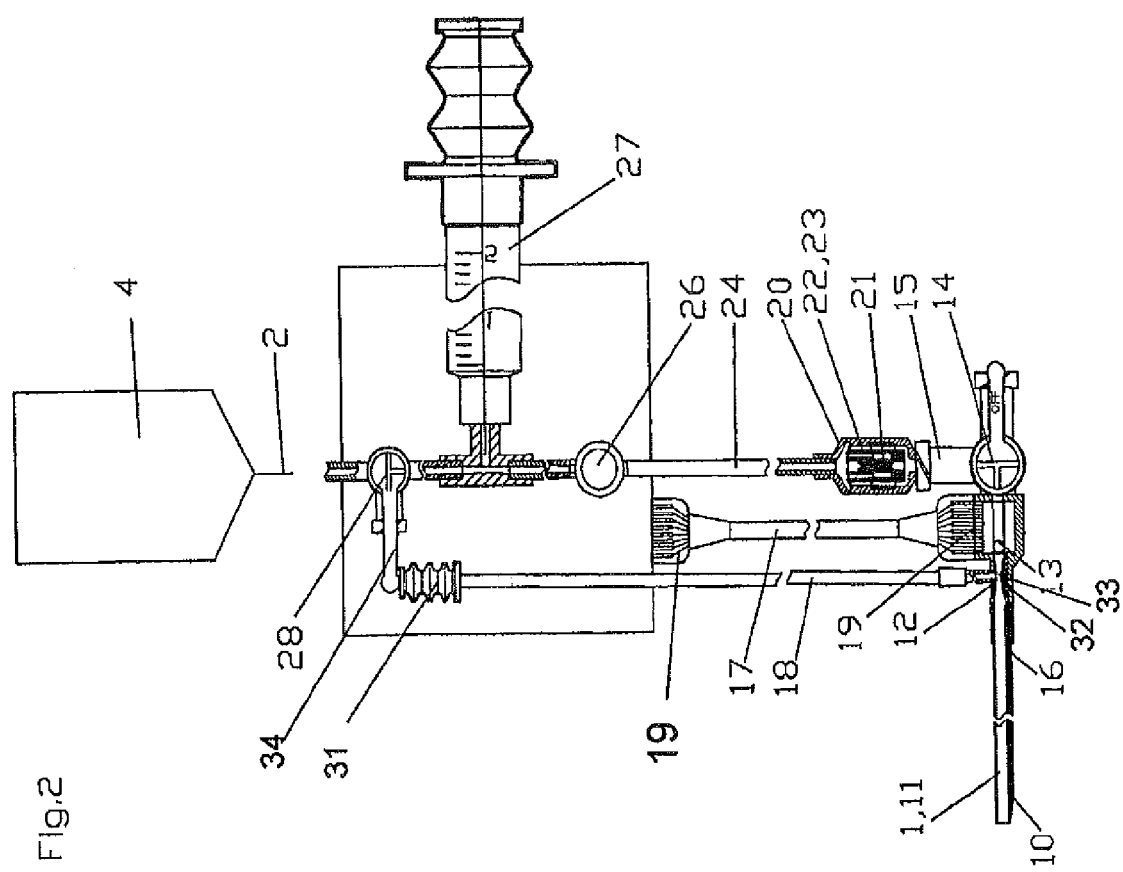

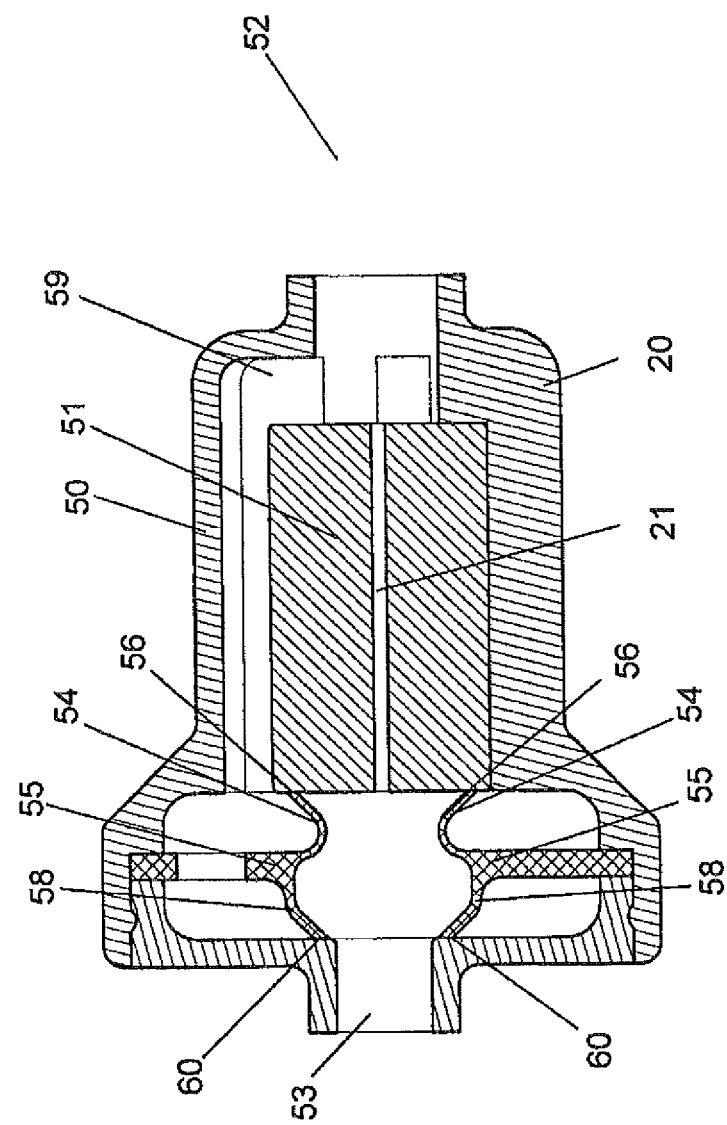

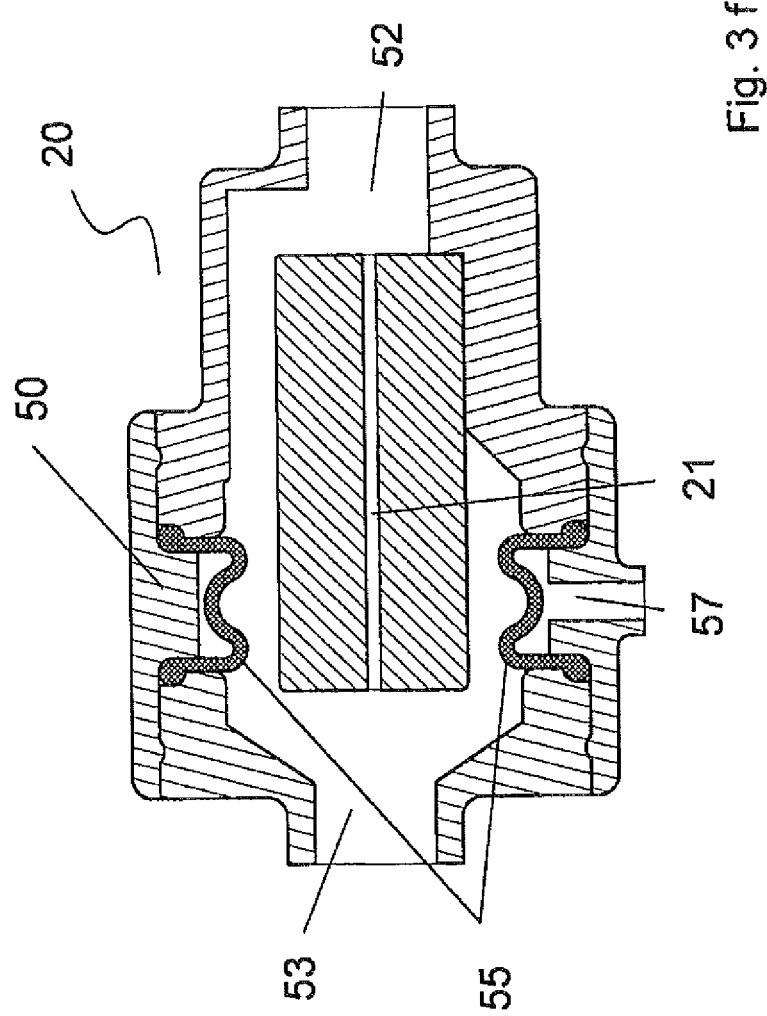

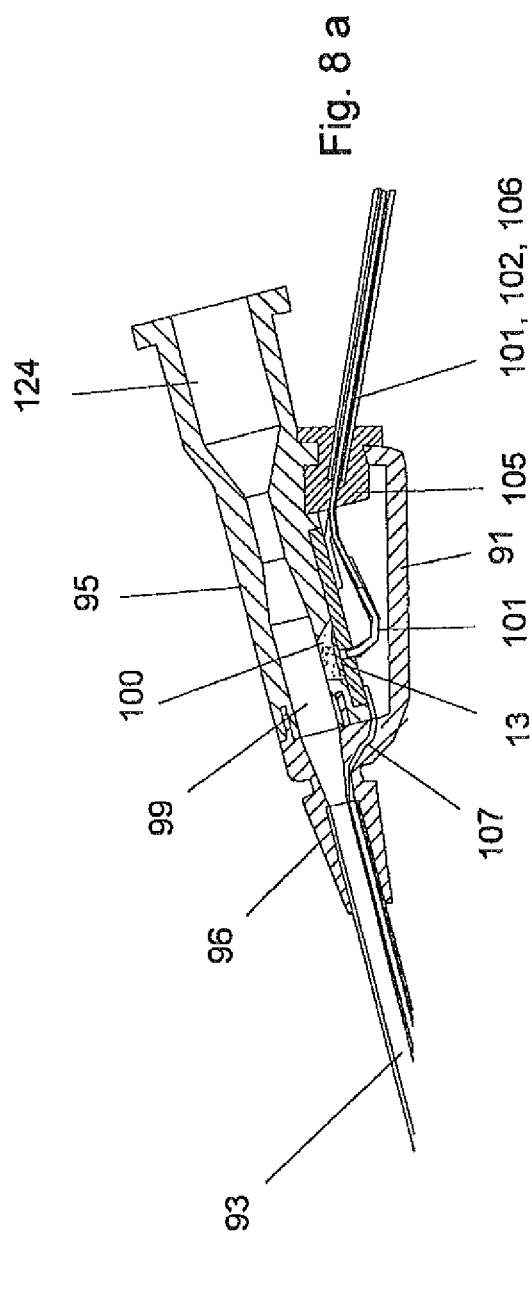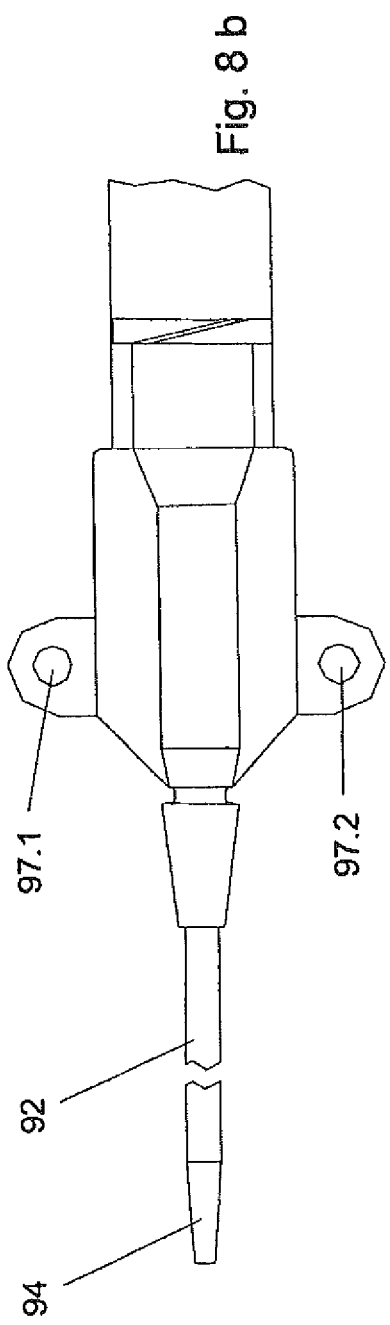

BLOOD VESSEL CATHETER AND INJECTION SYSTEM FOR CARRYING OUT A BLOOD PRESSURE MEASUREMENT OF A PATIENT

The present application is a continuation of U.S. patent application Ser. No. 11/637,546, filed Dec. 12, 2006 now abandoned entitled Blood Vessel Catheter and Injection System for Carrying Out a Blood Pressure Measurement of a Patient. It also claims priority to German application DE 10 2005 060079.4, filed Dec. 15, 2005, entitled Blood Vessel Catheter and Injection System for Carrying Out a Blood Pressure Measurement of a Patient, the entire disclosures of which are incorporated by reference herein.

The present invention relates to blood vessel catheter located proximate to a patient's body for measuring blood pressure, drawing blood samples or injecting fluids into a blood vessel of the patient. The present invention further relates to a system for drawing blood samples or injecting fluids into the blood vessel of the patient and for carrying out a blood pressure measurement of a patient.

BACKGROUND

Measurement systems for measuring blood pressure of a patient's body are well known in clinical appliances. They usually comprise a rinsing fluid reservoir which is connected using a fluid flow tube to a catheter tube, which in use penetrates a patient's body such that the rinsing fluid is supplied as a continuous rinsing fluid stream. Along the rinsing channel one or more valves can be arranged to manually stop the rinsing of the fluid into the patient's body.

The continuous measurement of a blood pressure of a patient is important to monitor the condition of ill patients. It is common that the measurement of the blood pressure is carried out using a single use pressure sensor and a rinsing system both mounted on an organizer plate. This organizer plate with the sensors is well accessible on heart level for the operator. The pressure sensor on this organizer plate is then connected to the patient via a long tube which is filled with liquid. Thus, the pressure signal is hydraulically transmitted via the transfer tube. Typically there is a 3 way stop cock between patient and pressure sensor for drawing blood samples Or injecting fluids.

The disadvantage of this system is that the pressure signal is falsified by the transfer characteristic of the long transfer tube system due to damping or resonance as a result of the length of the transfer tube.

As another possibility for measuring the blood pressure the use of a tip manometer is known. The tip manometer is located at the tip of the catheter tube such that in use the manometer is located inside the patient's body. Although such an arrangement provides a very good signal transmission it is very expensive and a larger diameter of the catheter tube is needed. Furthermore, controlling and adjusting the zero point pressure of the tip manometer is no longer possible after the catheter tube is placed inside the patient's body.

SUMMARY OF THE INVENTION

An object of the present invention is to provide a blood vessel catheter and a fluid transfer system which avoids the drawbacks of the prior art and allows for an accurate and continuous measurement of the blood pressure of the patient.

The present invention provides a blood vessel catheter and a fluid transfer system.

According to a first aspect of the present invention, a blood vessel catheter is provided for locating in close proximity to a patient's body and for injecting an injectate fluid into a blood vessel of the patient or drawing blood samples from the patient. The blood vessel catheter includes a catheter tube having a first end for penetrating the blood vessel of the patient and a pressure sensor which is arranged at a second end of the catheter tube outside of the patient, wherein the pressure sensor is adapted to sense a pressure of the liquid in the catheter tube as an indication of the blood pressure of a patient.

The catheter has an advantage that the pressure sensor for sensing the blood pressure of the patient is located close to the blood vessel of the patient such that a damping or a resonance of the detected pressure is reduced or eliminated. Furthermore, the pressure sensor is located outside of the patient's body such that a zeroing of the pressure sensor can be carried out even if the catheter is in use.

Preferably, the pressure sensor is further adapted to supply an electric pressure signal, wherein an electric interface is provided to releasably couple the pressure sensor to a reusable measurement unit. Thereby, the catheter is provided as a disposable item which can be further coupled to a disposable fluid transfer unit.

According to another embodiment of the present invention, a valve, especially a control valve, is provided which is arranged between the end of the catheter tube and the pressure sensor wherein the valve is adapted to be operated depending on a valve activation signal. A valve control interface may be provided to couple the valve with a remote valve control element.

Advantageously, the valve includes a squeezable tube portion having an adaptable lumen wherein the squeezable tube is provided in such a way to adapt the size of the lumen depending on a pneumatic or hydraulic valve activation signal.

According to a further embodiment, the valve may be coupled to the electric interface for receiving an electric valve activation signal.

Preferably, a connector is provided for coupling the catheter tube to a unit for rinsing, injection or drawing blood samples. This allows for the catheter to be provided as a disposable item which can be releasably coupled to a fluid transfer unit. Unlike the previous art this connector is close to the patient and preferably arranged upstream to the pressure sensor The present invention may further provide a shut-off valve arranged upstream to the pressure sensor which is adapted to be manually operated for controlling a liquid flow through the catheter tube. This allows an instant manual control of the fluid flow into the patient's body. For this valve also a 3 way stop cock could be used. This can allow convenient application of a guide wire to the catheter e.g. for a Seldinger catheter placement technique.

According to another aspect of the present invention a fluid transfer system is provided for rinsing the catheter or injecting an injectate fluid into a blood vessel of the patient or drawing blood samples from the patient and for carrying out a blood pressure measurement on a patient. The fluid transfer system includes a catheter tube having a first end for penetrating the blood vessel of a patient and a pressure sensor which is arranged close to a second end of the catheter tube, wherein the pressure sensor is adapted to sense a pressure of liquid in the catheter tube as an indication of the blood pressure of the patient.

The fluid transfer system according to present invention allows a continuous measurement of a blood pressure of a patient while the blood pressure is sensed close to the patient's body. A damping or a resonance of the pressure signal thus advantageously can be avoided.

According to an embodiment of the present invention, a measurement unit is provided which is electrically coupled to the pressure sensor for determining a pressure value.

Preferably, a control valve is arranged between the end of the catheter tube and the pressure sensor, wherein the control valve is adapted to be operated depending on a valve activation signal. Furthermore, the fluid transfer system includes a remote valve control element for providing the valve activation signal. The valve permits remote control of the fluid flow through the catheter tube.

Advantageously, a pneumatic signal activation line is provided to couple the valve to the valve control element wherein the remote valve control element provides a pneumatic or hydraulic valve activation signal.

Furthermore, it may be provided that the control valve includes a squeezable tube portion having a flexible lumen wherein the squeezable tube is provided in such a way to adapt the flexible lumen depending on the pneumatic or hydraulic valve activation signal.

According to a preferred embodiment of the present invention the fluid transfer system includes a reservoir for a rinsing medium, a fluid flow means coupled to the catheter tube, and a stop cock which is adapted to couple the reservoir to the catheter tube in a rinsing position.

Furthermore, the stop cock may be adapted to couple a reference pressure to the fluid flow means in a nulling position.

Moreover, the stop cock may be coupled to the valve control element in such a way that in the nulling position the valve is closed.

Preferably, the stop cock is adapted to cut off the fluid flow in the fluid flow means in a sampling position.

A fluid transfer system can be provided with a flow control unit having an upstream end which is coupled to a stop cock and a downstream end. The flow control unit includes a rinsing capillary for providing a predetermined flow of liquid through the fluid flow means, a first check valve adapted to open if a pressure difference between the upstream end and the downstream end of the flow control unit exceeds a predetermined first pressure value, and a second check valve adapted to open if a pressure difference between the downstream end and the upstream end of the flow control unit exceeds a predetermined second pressure value. Preferably the check valves are arranged in order that all fluid paths are reached by the rinsing streams through the capillary or the downstream check valve. In case the pressure sensor could not withstand the pressure generated during manual injection, the smallest cross section of the fluid path in the flow control unit is chosen smaller than the smallest cross section downstream the pressure sensor. This will reduce the pressure acting at the sensor position. Alternatively other pressure limiting means could be applied.

According to a preferred embodiment, a syringe is provided which is connected to the fluid flow means between the stop cock and the flow control unit for supply a bolus into the fluid flow means, e.g. for flush rinsing. Similar to state of the art blood sampling systems which are applied before the pressure sensor, blood samples could be drawn through the pressure sensor e.g. by:

Positioning the stopcock in sampling position.
Pulling the piston out of the syringe thereby removing rinsing fluid from the downstream fluid system.
Applying a needleless vacuum blood collection system to a blood sampling port, thereby drawing blood from the patient.
Removing the needleless vacuum blood collection system.
Pushing back the piston to the syringe, thereby refilling the rinsing fluid and cleaning the system.
Positioning the stopcock in rinsing position.

BRIEF DESCRIPTION OF THE DRAWINGS

Preferred embodiments of the present invention are now described in more detail with respect to the accompanying drawings in which:

FIG. 2 is a more detailed schematic view of a fluid transfer system according to the present invention;

FIG. 3 e-f show a cross-sectional view of a flow control unit arranged in the fluid flow path of the fluid transfer system according to a another preferred embodiment.

FIGS. 8a and 8b are a cross-sectional view from two sides of a catheter as shown in FIG. 7.

DETAILED DESCRIPTION

Figure 1:
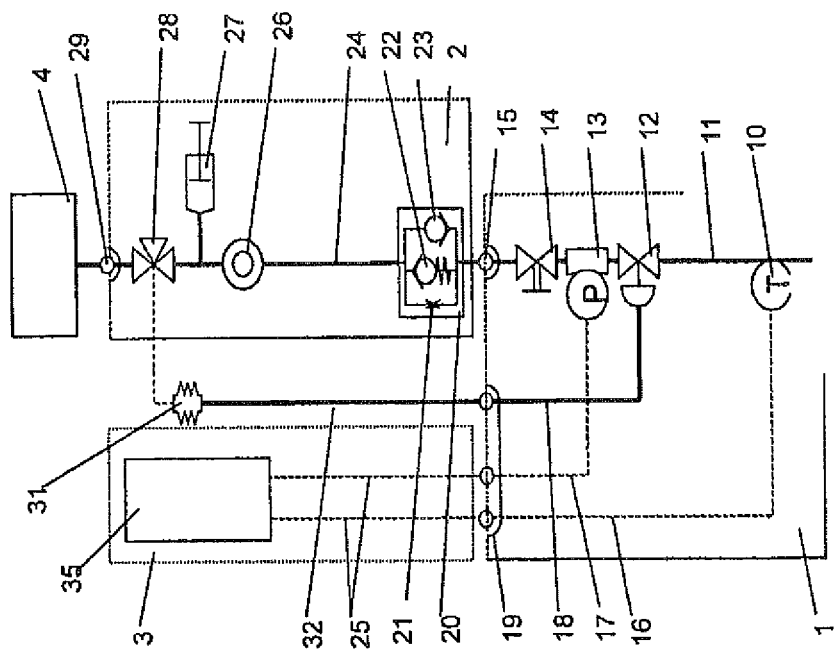
FIG. 1 is a schematic view of one embodiment of a fluid transfer system according to the present invention.

FIG. 1 shows a schematic view of a fluid transfer system for supplying an injected fluid into a patient's body. The fluid transfer system includes a blood vessel catheter unit 1, a fluid transfer unit 2, an operational unit 3, and a reservoir 4 for supplying a rinsing fluid. The blood vessel catheter unit 1 and the fluid transfer unit 2 may be coupled by a first interface 15 and the blood vessel catheter unit and the operational unit 3 are coupled by a second interface 19. Furthermore, the fluid transfer unit 2 may include a third interface 29 for coupling with the reservoir 4.

The blood vessel catheter unit 1 includes a catheter tube 11 having a tip end for penetrating a blood vessel of the patient's body. At another end of the catheter tube 11 a control valve 12 is arranged to cut off the flow of the injected fluid through the catheter tube 11 depending on an activation signal. The activation signal can be applied as a pneumatic, hydraulic or electrical signal. In the illustrated embodiment the activation signal is supplied to the control valve by means of a pneumatic valve activation line 19 which is coupled by means of the second interface 19 with a valve control element 31. The valve control element 31 can be designed as a bellow to provide a pressure for controlling the control valve.

The catheter tube 11 can be provided with a temperature sensor 10. Temperature sensor signal lines 16 are coupled to the second interface 19. The operational unit 3 which may be coupled to the second interface 19 is designed for measuring the temperature. The temperature sensor 10 is preferably located at a portion of the catheter tube 11, e.g. the tip, which is located inside the patient's body while in use.

Upstream to the control valve 12 a pressure sensor 13 is coupled to the lumen of the fluid channel within the catheter unit 1. The pressure sensor 13 supplies an electrical pressure signal via electrical pressure signal lines 17 to the second interface 19 such that the electric pressure signal can be received by the operational unit 3 for detection. The pressure sensor 13 determines the pressure of the liquid within the lumen of the fluid channel as an indication of the blood pressure of the patient. Usually, the pressure of the liquid in the fluid channel substantially corresponds to the blood pressure of the patient. Thus, the second interface 19 includes ports for connecting the temperature signal lines 16, the pressure signal lines 17 as well as the pneumatic valve activation line 18.

The blood vessel catheter unit 1 may further comprise a cut-off valve 14 for manually cutting off the fluid stream through the catheter tube 11.

Upstream to the cut-off valve 14, the first interface 15 is located which is provided as a connector 15. The connector 15 serves for a releasably coupling the fluid transfer unit 2 to the blood vessel catheter unit 1 such that the rinsing fluid can flow from the fluid transfer unit 2 to the catheter unit 1. By providing the second interface 19 and the connector 15, the blood vessel catheter unit 1 can be completely released from the operational unit 3 and the fluid transfer unit 2. This allows that the catheter unit 1 and the fluid transfer unit 2 can be designed as a disposable item while the operational unit 3 may e.g. be designed for repeated use.

The fluid transfer unit 2 includes a fluid flow means or section 24 on which from upstream to downstream a stop cock 28, a syringe 27, a blood sample port 26, and a flow control unit 20 are arranged. On the upstream end of the fluid flow means 24 as the third interface a reservoir connector port 29 is provided which serves for applying the reservoir 4 including the rinsing fluid to be supplied to the patient.

The stop cock 28 can be placed into three positions:

In a first rinsing position the reservoir 4 is connected to the fluid flow means 24 such that the injectate fluid flows via the fluid flow means and the connector 15 to the blood vessel catheter unit 1 to supply the injectate fluid to the patient.

In a nulling position the stop cock 28 applies on the fluid in the fluid flow means 24 a predetermined pressure reference, preferably an atmospheric pressure of an outer environment. Via the fluid flow means 24 the predetermined pressure reference is applied to the catheter unit 1. Therein, the predetermined pressure reference is used to calibrate the pressure sensor 13.

In a sampling position the stop cock 28 is closed to cut off the fluid flow means 24 from the reservoir 4 as well as from the pressure reference. This position may be used to draw a blood sample via the blood sample port 26. The syringe 27 could be used to remove the rinsing fluid from the catheter unit 1 and the fluid transfer unit 2 and release it back after the blood sample is drawn. In the sampling position also for flush rinsing a bolus can be applied to the patient using the syringe 27.

To apply the pressure reference onto the pressure sensor 13 of the catheter unit 1 it is necessary that the control valve 12 is closed such that no fluid can flow through the catheter tube 11. This is achieved by applying the activation signal on the pneumatic valve activation line 18. Furthermore, a calibration signal can be generated by the stop cock 28 which is applied to the operation unit 3 such that a calibration measurement of the pressure in the catheter unit 1 can be initiated automatically.

The flow control unit 20 is designed to permanently allow a rinsing fluid flow though a capillary 21 which has a predetermined flow rate e.g. of 3 ml/h. To allow that the rinsing fluid could be removed and blood samples could be taken via the connector 15 the flow control unit 20 has to provide a bypass which is formed by a first check valve 23. The first check valve 23 opens if a pressure between a downstream end, e.g. at the connector 15, and an upstream end excites a predetermined first threshold pressure. This threshold is chosen at a low negative value e.g. 10 mmHg in order not to damage blood cells. The pressure difference can for example be achieved by the syringe 27 or by connecting a syringe 26 to the blood sample port 26 and by applying an underpressure onto the fluid flow means 24. The flow control unit 20 includes a second check valve 22 which opens if at least a second threshold pressure is applied from upstream to downstream for example if a bolus is injected into the fluid flow means 24 which shall be dispensed to the patient. This threshold is chosen at a positive value greater than the pressure usually applied to the fluid reservoir 4 e.g. 500 mmHg.

In FIG. 2 a more detailed view of the fluid transfer system is illustrated. With regard to the blood vessel catheter unit 1 it is shown that the catheter unit 1 is integrally formed as the interface 19, the connector 15 and the pneumatic valve activation line 18 which are releasably connectable to the fluid transfer unit 2 and the operation unit 3.

In the detailed view, it can be seen that the control valve 12 of the catheter unit 1 is designed as a squeeze valve which can be controlled by means of a pneumatic activation signal that is applied onto a flexible tube 32. An increasing pressure within the pneumatic signal activation line 18 results in that the lumen of the flexible tube 32 is reduced and finally cut off such that a main flow path 33 within the control valve 12 is closed. By releasing the overpressure within the pneumatic signal activation line 18 the blood pressure of the patient within the main flow path 33 results in that the flexible tube 32 opens such that the rinsing fluid is able to flow again through the catheter tube 11 into the patients body. In a preferred embodiment of the present invention, a low or even negative pressure gradient is applied to the pneumatic signal activation line 18 in order to force the flexible tube 32 to be extended and forced at the inner wall of the main flow path 33. Thus, it is ensured that the flexible tube is not even partly blocking the way of the main flow path and thus the control valve 12 is fully opened again.

Generally, the control valve 12 can be remote controlled via the pneumatic signal activation line 18 and may be coupled to the stop cock 28 such that the overpressure is applied to the control valve 12 if the stop cock 28 is positioned in the nulling position.

In one embodiment, the stop cock 28 may comprise a pivotable inner member which provides a cutting off of the fluid flow connection between the reservoir 4 and the fluid flow means 24 and a connection between the fluid flow means 24 and the pressure reference depending on the position of the inner member. The pivotable inner member is provided with a lever 34 which activates the valve control element 31 in form of the bellow such that the bellow is squeezed and an overpressure in the pneumatic signal activation line 18 is obtained. In other positions the lever 34 releases the bellow 31 such that the pressure within the pneumatic signal line relieves resulting in the control valve opening again.

According to other embodiments the control valve 12 can be electrically or mechanically activated and deactivated in a remote mariner.

In the nulling position the control valve 12 is closed and the fluid flow means 24 is opened to the pressure reference such that the pressure sensor 13 can be calibrated even if the catheter tube II penetrates the blood vessel of the patient. Furthermore, the close coupling of the pressure sensor 13 with the catheter tube 11 allows for a continuous measuring of the blood pressure while the damping and resonance effects are reduced.

The second interface 19 is adapted to be coupled to the operational unit 3 via an appropriate plug such that an electronic monitoring unit 35 can continuously monitor the blood temperature and the blood pressure of the patient.

Figure 3:
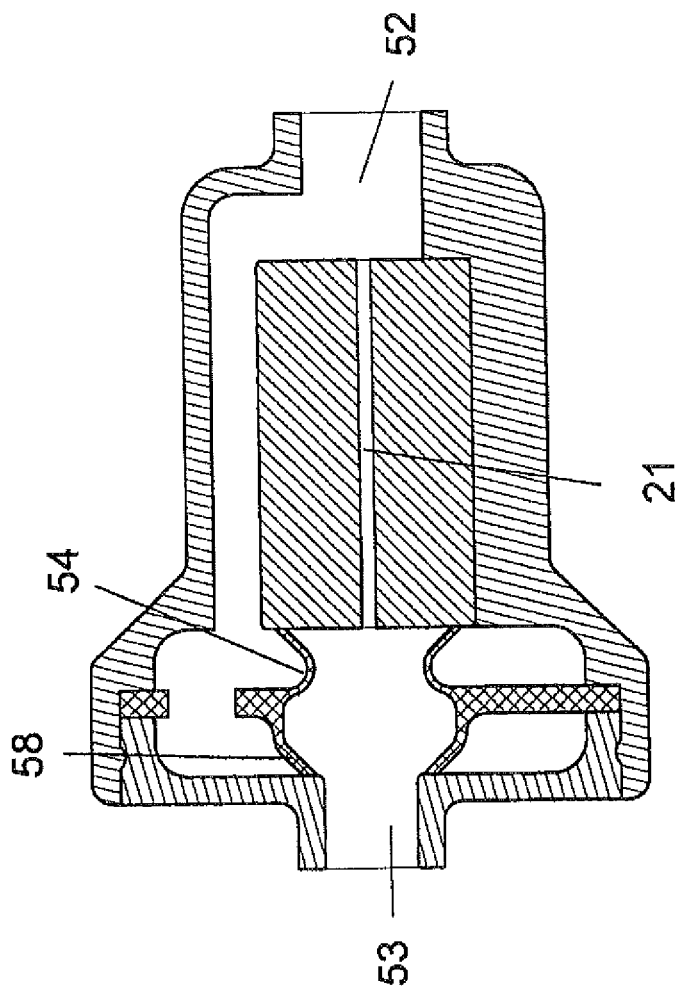
FIG. 3 a-d show a cross-sectional view of a flow control unit arranged in the fluid flow path of the fluid transfer system according to a preferred embodiment.
Figure 3:
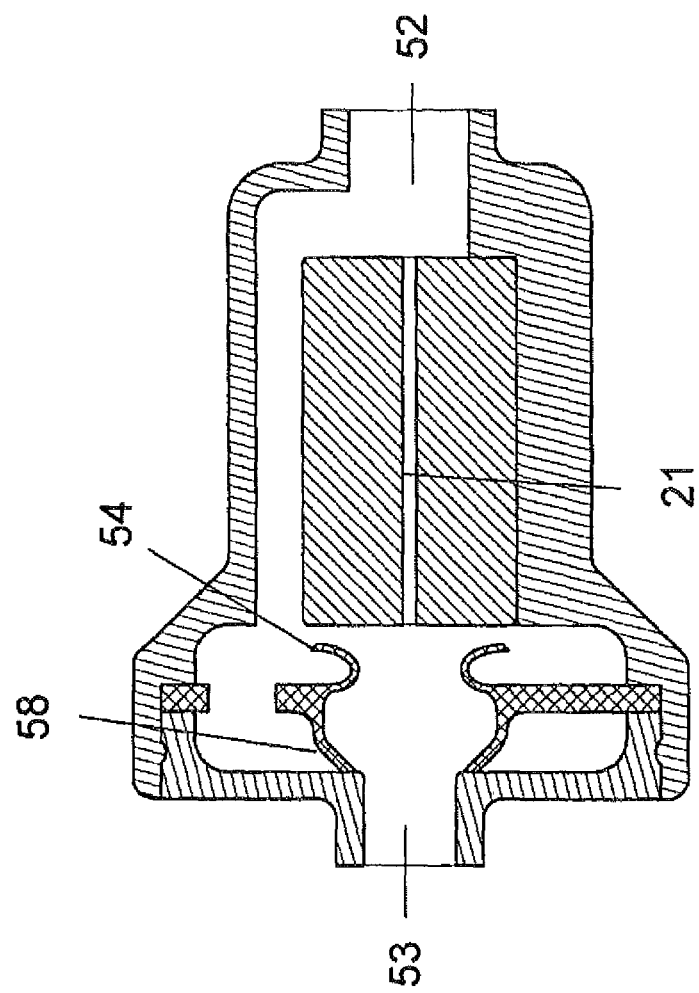

In FIGS. 3 a to d, a preferred embodiment of the flow control unit 20 is shown. The flow control unit 20 includes a housing 50 in which a rinsing capillary 51 included in a capillary body 59 is arranged which provides a small flow path from an upstream port 52 to a downstream port 53 of the flow control unit 20. The flow path has a small lumen adapted to maintain a constant predetermined rinsing flow rate of e.g. 3 ml/h. The first check valve 23 (FIG. 2) includes a first flexible member 54 a first end of which is fixedly attached at a support element 55. A second end of the first flexible member 54 abuts a stop area 56 of the capillary body 59 if no additional pressure is applied. If an increased pressure between the upstream and the downstream port 52, 53 of the flow control unit 20 is applied the overpressure also acts on the first flexible member 54 which opens if a first threshold pressure is exceeded.

The first flexible member 54 is usually closed and may be provided having an "umbrella behavior", i.e. if the first threshold pressure is exceeded the first flexible member 54 flaps such that the second end of the first flexible member 54 is instantly removed from the stop area 56 and a fluid channel is established between the upstream and the downstream port 52, 53 of the flow control unit 20. The lumen of the established fluid channel has a size which allows a flow rate which is essentially larger than the rinsing flow rate through the capillary 51.

Similarly, a second check valve 22 (FIG. 2) is arranged which includes a second flexible member 58 which is attached with a first end to the support element 55 and which abuts with a second end on an inner stop area 60 of the housing 50. Therefore, the second check valve 22 is usually closed. It remains closed if a positive pressure difference between the upstream and the downstream port 52, 53 of the flow control unit 20 is applied. If a positive pressure difference between the downstream port 53 and the upstream port 52 is applied the second flexible member 58 may flap. The second flexible member 58 is adapted that it flaps if a pressure between the downstream port 53 and the upstream port 52 excites a second threshold pressure. Thus, one exemplary embodiment of a flow control unit 20 having the aforementioned functionality can be realized.

Figure 3D:
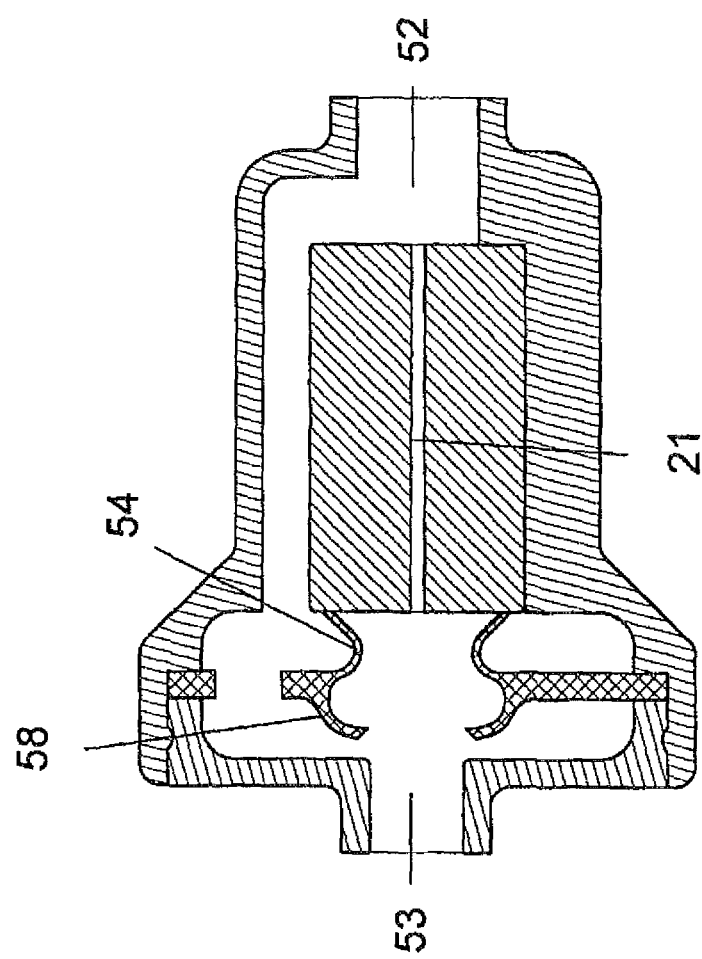

In FIGS. 3b to 3d the mechanism is illustrated for these three basic situations. In FIG. 3b flow through the capillary 21 takes place whereas a threshold pressure is not exceeded.

In FIG. 3c the situation is illustrated where the first threshold pressure is exceeded and the first flexible member 54 flaps such that the second end of the first flexible member 54 is instantly removed from the stop area 56. This is the situation when a pressure difference exists where the higher pressure is applied from the downstream port 53.

The other situation is illustrated in FIG. 3d. Herein, a pressure from the upstream port is applied which causes a pressure difference between the upstream port and the downstream port in favor of the upstream port which exceeds the threshold. Thus, the second flexible member 58 flaps to give way whereas the first flexible member 54 is pressed against the wall.

Figure 3E:
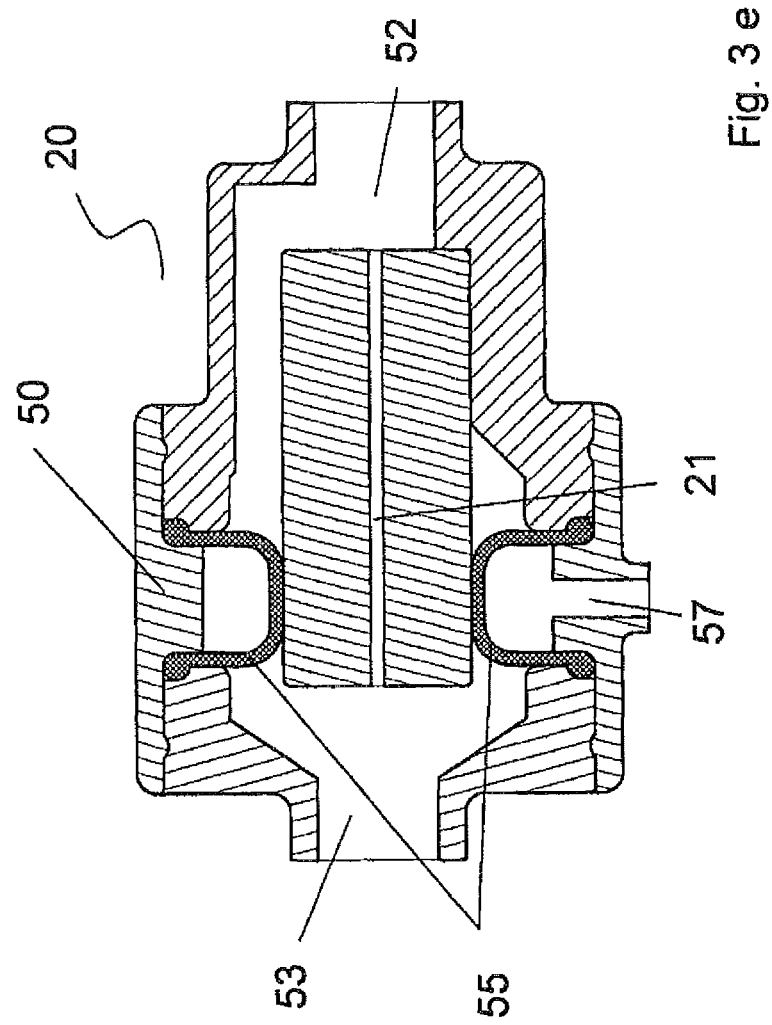

In FIGS. 3e and 3f, two situations for another embodiment of the flow control unit 20 are illustrated. In this embodiment, flexible member 55 in form of a ring is provided in the circumference of the housing 50. This flexible member 55 is adapted to close the lumen between the downstream port 53 and the upstream port 52. This is accomplished by flexible member 55 being pressed against the outer wall of the member with capillary 21. Thus, in the situation of FIG. 3e flow between the upstream port 52 and the downstream port 53 is only possible via the capillary 21. In order to ensure that the flexible member 55 closes the lumen, a pressure is applied onto a medium through inlet 57. By means of this pressure applied, the flexible member 55 is pressed against the member comprising the capillary 21.

In FIG. 3f a second situation is shown as in FIG. 3e whereas now negative pressure is applied to the inlet 57. Thus, the flexible member 55 is deflated and thereby gives path for flow between the upstream port 52 and the downstream port 53. The actuation of the flexible member 55 to give free this path can be controlled remotely by applying the respective negative pressure. Thus, in both cases of flow from upstream port 52 to downstream port 53 or flow from downstream port 53 to upstream port 52 the flexible member 55 can be switched from the situation in FIG. 3e (closed) to the situation in FIG. 3f (open). The opening activation signal could be derived from the nulling and sampling position of stop cock 28.

Figures 4A, 4B:
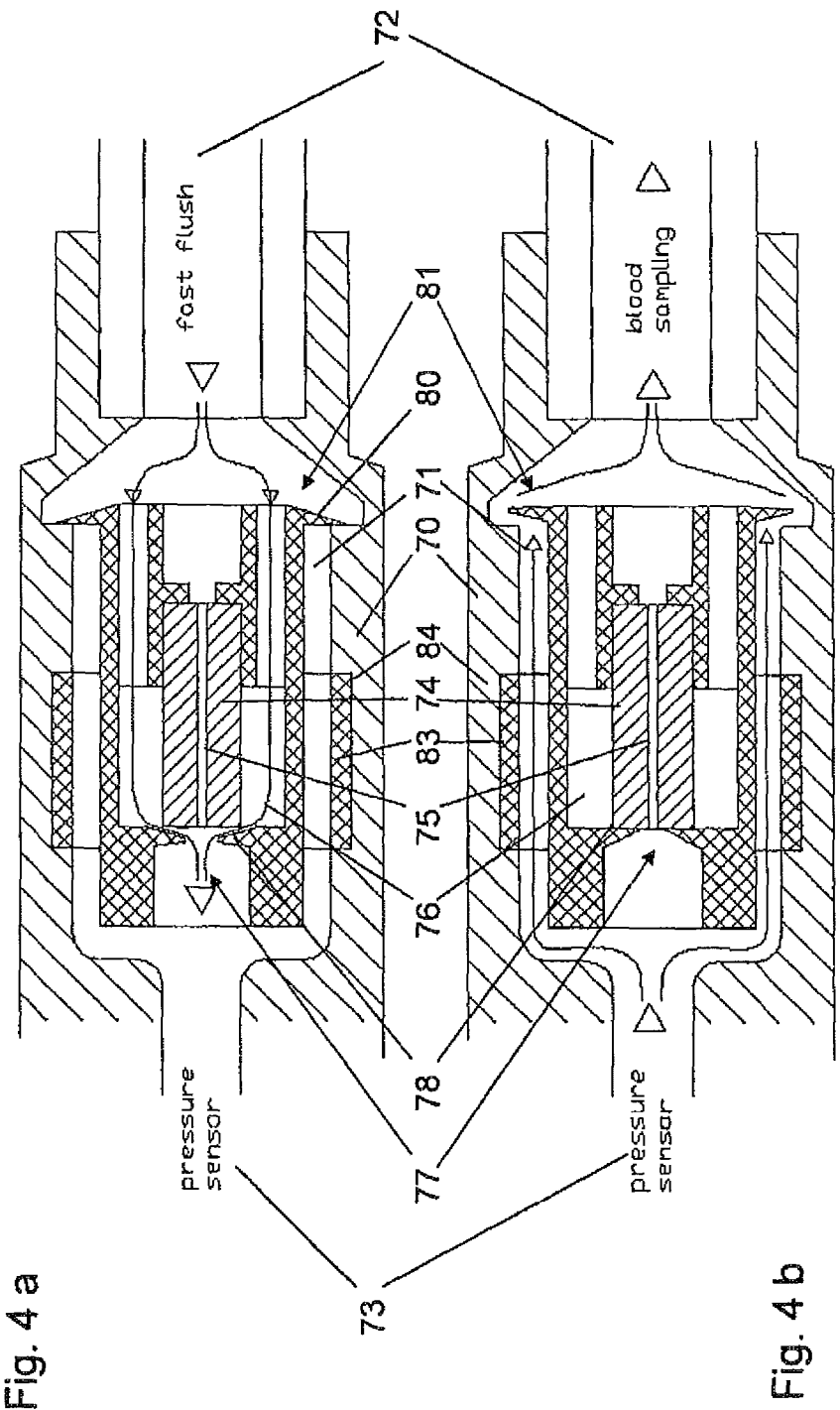
FIGS. 4a and 4b show a cross sectional view of another embodiment of a flow control unit for use in the fluid transfer system according to the present invention in a first and a second operational condition.

In FIGS. 4a and 4b, another embodiment of the flow control unit is illustrated. The flow control unit includes a housing 70 having an upstream port 72 and a downstream port 73. Inside the housing 70 a rinsing capillary 75 is arranged in a capillary body 74 to provide a rinsing flow channel which is permanently opened. Neighboured to the capillary body 74 a first flow path or channel 76 is arranged which leads to a first check valve 77 having first flexible members 78 which are adapted to flap if the pressure between the upstream port 72 and the downstream port 73 exceeds a first threshold pressure. FIG. 4a shows a condition wherein the first threshold pressure is exceeded by the applied pressure such that the first flexible members 78 are flapped such that a fluid channel between the first flow path 76 and the downstream port 73 is established.

Furthermore, a second flow path 71 is provided which leads from the downstream port 73 to a second check valve 79 which includes second flexible members 80 one and of which in a closed condition abut the stop area 81 which is integrally formed with the housing 70. If a pressure difference between the upstream port 72 and the downstream port 73 exceeds a predetermined second threshold pressure the second flexible members 80 flap such that the free ends of the second flexible members 80 are removed from the stop area 81 such that a flow channel between the second flow path 71 and the upstream port 72 is established. This condition is shown in FIG. 4b.

The first and second flexible members are preferably arranged such that they snap if a pressure to which they are subjected exceeds a threshold pressure. The snapping of a valve is also known as an umbrella effect.

The first and second flexible members 78, 80 are preferably included in an integral element 81 which is formed as a flexible part and can be introduced in the housing 70. The integral element 81 may comprise an engagement member 83 which engages in a recess 84 of the housing 70 when inserted.

As a result, a pressure measuring system with an improved signal transfer behavior and a simple handling is provided.

The present invention includes a disposable catheter 1 with integrated pressure sensor 13 connected to a remote disposable unit 2 (fluid transfer unit) and a remote reusable unit 3 (operational or measurement unit). Since the catheter is usually accessible for maintenance only with difficulty, the necessary operations after placing the catheter like rinsing, drawing blood samples and zeroing the pressure sensor are remotely operated. Preferred this is achieved by a preferably pneumatically operated control valve 12 and/or pressure dependent check valves 22, 23. For measuring and adjusting the zero point pressure a remotely controlled valve 12 is arranged before the pressure sensor 13. This is preferably a pneumatically activated stop cock or a squeeze valve. For practical reasons a hand operated shut-off valve 14 can be attached after the pressure sensor 13.

The pressure sensor 13 and the valves 12, 14 and the connector 15, are preferably arranged in a single rigid housing at the end of the catheter tube 11 and located outside of the patient. For catheter placement the pressure sensor 13 and all firmly connected valves 12, 14 preferably possess a straight free passage, by which a guide wire can be introduced through the catheter lumen 11. Frequently also a blood temperature sensor 10 is needed. Therefore, preferably a thermistor is located at the tip of the catheter 1 and is in thermal contact to the streaming blood of the patient. The thermistor wires (temperature sensor signal lines) 16 are placed in the same catheter tube however in a separate lumen. Preferably the thermistor wires 16, the pressure transducer wires (electrical pressure signal lines) 17 and the pneumatic valve activation line 18 are connected by an interface, preferably a single plug 19 which is integrated in the mentioned rigid housing.

Usually, such catheters need a constant small flow (3 ml/h) of a rinsing solution. In order that this rinsing system 2 does not damp the pressure signal, preferably immediately after the catheter connection 15 a capillary 21 is attached. Because at the same connection also blood samples could be taken or flush rinsing could be performed, the capillary 21 could be bypassed dependent on the differential pressure by check valves 22, 23. Check valve 22 opens if the pressure in the rinsing system is 500 mmHg above the blood pressure in the catheter 1. Check valve 23 opens if the pressure in the rinsing system is 10 mmHg below than blood pressure in the catheter 1. The capillary 21 and the check valves 22, 23 are preferably arranged in a single housing 20 and the functions are preferably performed in a single part. In a further embodiment, a flexible tube 24 of appropriate length extends from the housing 20 to a blood sample port 26, a syringe 27 and a hand operated stop cock 28. All of them are preferably located on a bedbox at a convenient place for the operator. The stop cock 28 is preferably at the level of the heart.

The stop cock 28 is preferably adapted to be placed in three positions: Rinsing position—by connecting fluid reservoir 4 to catheter 1. Nulling position—by connecting atmosphere to catheter 1. Sampling position—by closing all ports. Forcing stop cock 28 in nulling position preferably also mechanically activates a bellow 30 which activates the valve 12 simultaneously via a pneumatic signal line 32.

Preferably, the interface plug 19 is connected to the sensor electronic 33 by electric signal lines 25. As usual the fluid reservoir 4 is held at 300 mmHg using a wristband.

Figure 5:
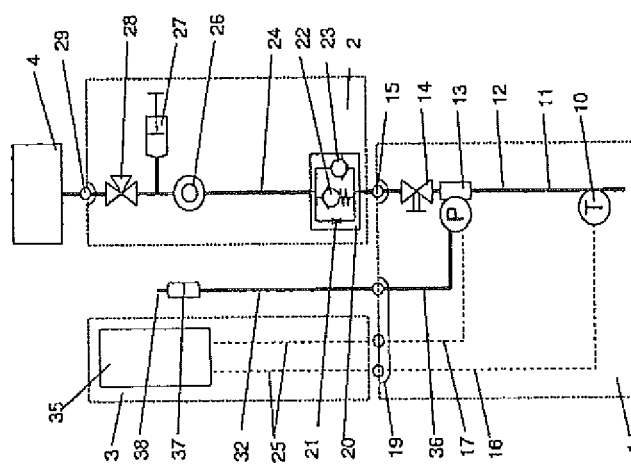
FIG. 5 is a schematic view of another embodiment of the fluid transfer system according to the present invention.

In FIG. 5 another schematic view of one embodiment of an injection system according to the present invention is shown. This view is similar to the design as shown and described in FIG. 1. In the embodiment of FIG. 5, however, a pressure sensor 13 is provided that is connected to a tube 32 filled with liquid or gel. This tube 32 has at its end a reservoir 37. The other end is connected via the second interface 19 to the blood vessel catheter unit 1. Especially, the tube 32 is connected to a tube 36 within the blood vessel catheter unit 1. Thus, the pressure of the liquid column in tube 32 acts on the pressure sensor via tube 36. As a result, the pressure sensor is acted upon the pressure difference of the pressure within the catheter, i.e. the patient, and the pressure within the column of tube 32. Tube 32 and the reservoir 37 are arranged such that the reservoir is on the same height as the heart of the patient. Thus, the pressure difference measured by the pressure sensor is the pressure within the catheter, i.e. the patient, corrected by the offset caused by the location of the pressure sensor away from the heart. Thus, the pressure at the pressure sensor is the pressure as present in the patient in the heart region. In pressure sensors of the prior art, this offset has to be calculated and the read out of the pressure sensor has to be corrected mathematically to give the value of the pressure in the heart region. As an advantage of the present arrangement, this pressure sensor does not have to be calibrated and set to atmospheric pressure since it already shows the correct difference, i.e. the result which is usually calculated via the absolute pressure and correction data taking into account the distance of the catheter to the heart.

Figure 6:
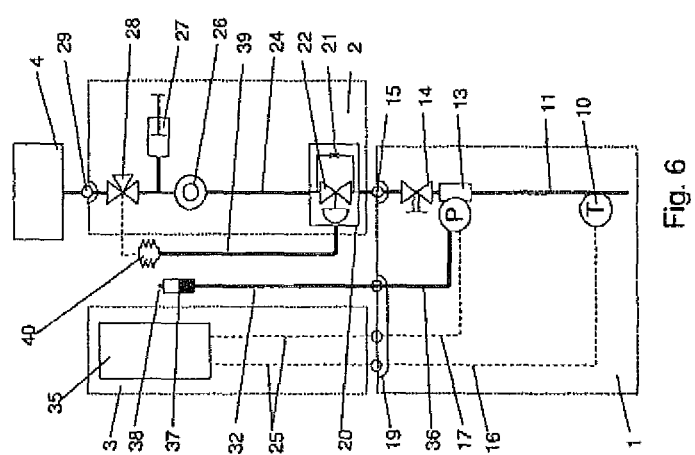
FIG. 6 is a schematic view of another embodiment of the fluid transfer system according to the present invention.

In FIG. 6, a schematic view of another embodiment of the injection system according to the present invention is shown. This assembly is the system as described in FIG. 5 additionally providing a remote control and actuation device 40 to operate the flow control unit 20.

This arrangement is preferably used when using a flow control unit 20 as shown in FIGS. 3 *e* and 3 *f*. The opening activation signal could be derived from the nulling and sampling position of stop cock 28 which is operating a bellow 40. Thus, it is possible to remotely control the flow control unit 20 and to open the fast flush lumen or to close it. This is accomplished similar as the activation of the valve control element 31 in FIG. 1.

Figure 7:
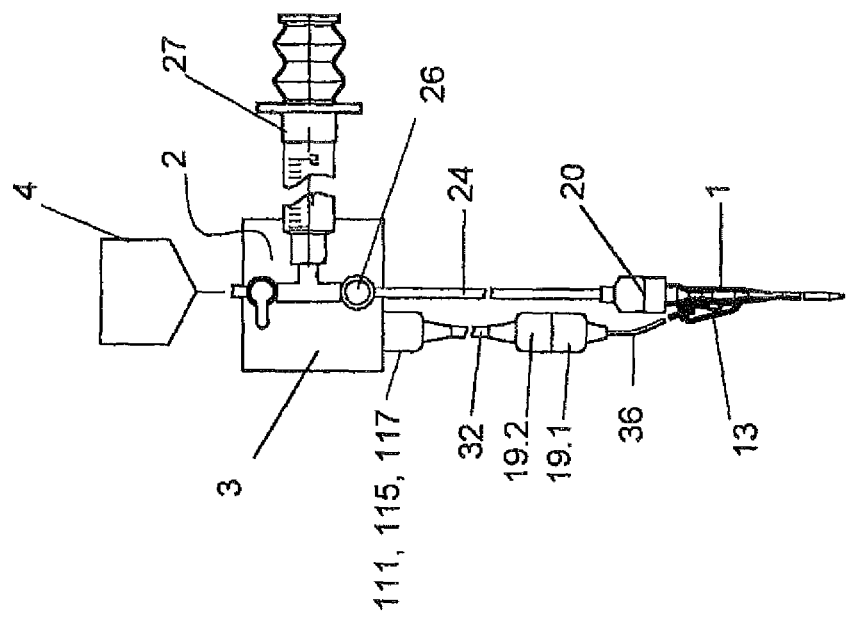
FIG. 7 is a more detailed schematic view of another fluid transfer system according to the present invention.

In FIG. 7, a more detailed schematic view of another fluid transfer system according to the present invention is shown. This arrangement is applicable with the system as shown in FIG. 5.

A pressure sensor 13 is arranged next to a catheter 1 having a lumen to which the pressure sensor 13 is connected. Further, an interface 19 comprising two connectors 19.1 and 19.2 being connectable to each other is provided. The pressure sensor 13 is connected to the connector 19.1 via line 36. The connector 19.2 is connected to the measurement unit 3 via line 32. Line 32 includes a line filled with liquid building a liquid column, and is connected to the measurement unit 3 via a pressure channel 111 with a hydrophobic membrane 115, and a connector 117 such as an electrical monitor circuit plug. As a result, the pressure of the liquid column within line 32 acts upon the pressure sensor via the interface 19 and line 36.

The catheter is further connected to a rinsing and blood sample system 2 by a line 24, the blood sample system 2 having a syringe 27 and a blood sample port 26. Between catheter 1 and the rinsing and blood sample system 2 a flow control unit 20 is provided. This flow control unit 20 includes a capillary 21 (see FIG. 1) thus allowing a rinsing of fluid from the fluid reservoir 4 into catheter 1. Further, the flow control unit 20 allows for fast flush and blood sampling as described above, especially with respect to the flow control units 20 as described in FIGS. 3 *a* to 3 *f*.

When working, the measurement unit 3 will be situated at the same height as the heart of the patient. Thus, the fluid column within line 32 will act upon the pressure sensor from the one side and the pressure within the lumen of catheter 1 will act upon the pressure sensor 13 from the other side. The pressure sensor 13 will then read out the difference of the two pressures, i.e. the pressure at the heart region of the patient as corrected by the pressure applied in line 32.

In FIGS. 8a and 8b, cross-sectional views from two sides of the catheter 1 as shown in FIG. 7 are illustrated.

The catheter 1 includes a housing 95 with a catheter tube 92 arranged at the distal end of the housing 95 comprising an inner lumen 93. The catheter tube 92 is connected to the housing via a bend protection 96. At the proximal end of the housing, a luer access 124 is provided.

In the housing 95 a pressure sensor 13 is arranged next to a pressure channel 99 (which is filled with liquid) extending from the inner lumen 93. The pressure sensor 13 is connected to the pressure channel 99 via a transmission membrane 100, preferably made of gel. On the other side, the pressure sensor is connected to a pressure channel 101. The pressure channel 101 is attached to a strain relief 105. Within the strain relief 105, other circuits like the pressure channel 101, a connection cable 102 and electrical circuits 106 are integrated. The pressure channel 101 is filled with a pressure transmitting material, for instance gel or water emulsions. Within the housing 95 further sensors 107 like a temperature sensor is integrated.

With such an arrangement, the pressure sensor 13 is subjected to a pressure difference between the pressure in the pressure channel 99 and the pressure from pressure channel 101 acting upon the pressure sensor 13.

Further, the pressure sensor is kept out of the way of the inner lumen. Thus, a guide wire to be inserted into the inner lumen can not be brought into contact with the pressure sensor and damage the pressure sensor. It is advantageous to choose the angle of the pressure channel 99 within the housing in such a way that the housing 95 additionally protects the catheter tube 92 from damages by bending. Further, the housing 95 provides for an advantage distance between the luer access 124 from the skin of the patient. Preferably, the housing 95 includes a base plate 91 that can be placed on the skin of the patient. In combination with a bend protection 96 which itself is preferably bendable, a good protection for the catheter tube 92 is provided.

In FIG. 8b a view onto catheter 1 is illustrated. At the distal end of the catheter tube 92, a conical formed tip 94 is provided. The housing further includes suture eyes 97.1 and 97.2 for fastening the housing to the skin of the patient.

Figure 9:
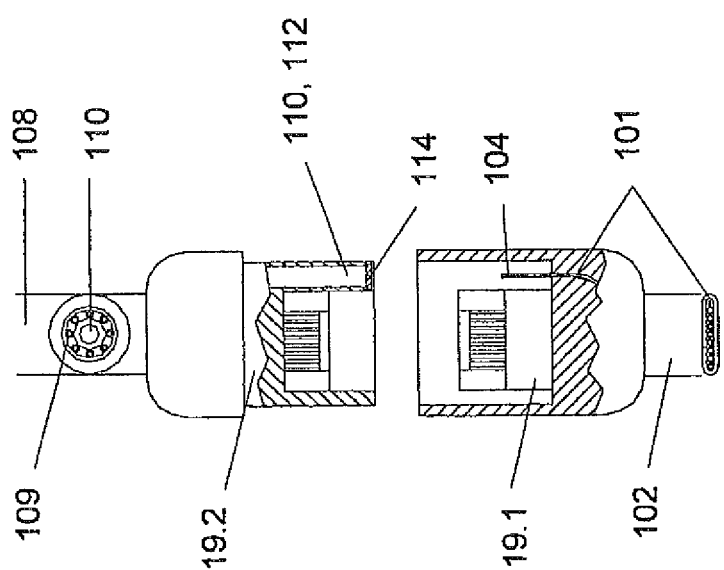
FIG. 9 is a more detailed view of the interface as shown in FIG. 7.

In FIG. 9 a more detailed view of the interface 19 as shown in FIG. 7 is illustrated.

The interface 19 includes two connectors 19.1 and 19.2. The connector 19.1 is connected to the blood vessel catheter unit 1 whereas the connector 19.2 is connected to the measurement unit 3. A connection cable 102 coming from the catheter unit 1 includes different circuits and a pressure channel 101 coming from the pressure sensor 13 as indicated in FIG. 8a. The interface connector 19.1 is made as a plug matching to the counter part interface connector 19.2. The pressure channel 101 forms a puncture spike 104 within the first interface connector 19.1. This puncture spike is preferably made of a thin, bendable tube out of Nitinol. At the other side, a puncture membrane 114 is provided. This puncture membrane closes a water column 110 towards the second interface connector 19.2. This puncture membrane can be made of elastic material, for instance silicon discs, already comprising a puncture which is long enough to prevent water to flow through the long puncture within the elastic material. Thus, no water from the water column 110 can flow out. In the upper part of the second connector 19.2, the electrical circuits 109 are provided around the water column 110 within the monitor cable 108.

When the two connectors 19.1 and 19.2 are put together, the electrical circuits of the connectors 19.1 and 19.2 will be plugged together. Further, the puncture spike 14 will penetrate the puncture membrane 114 thus giving way between the fluid medium, preferably gel, of the pressure channel 101 and the water column 110. Since within the puncture membrane 114 there was already provided a puncture, the puncture membrane is not inflicted. Thus, when separating the two connectors 19.1 and 19.2 from each other again, the puncture membrane 114 will again close the water column 110.

The other end of the water column 110 is either open or protected by a hydrophobe membrane 115 (FIG. 7) which is permeable to air and not permeable to water to avoid loss of water. This other end of the water column 110 is situated at the height of the heart. Thus, the pressure sensor will output the correct difference of pressure with respect to the location of the heart. Preferably, the inner diameter of the water columns 110 is chosen so small that the water is additionally hindered to flow out because of these dimensions. The other end of the water column can be fixed at the height of the heart by integrating the water column 110 within the monitor cable 108 or an electrical monitor circuit plug which is connectable to a so called monitor-bed-box. On the front plate or panel of this monitor-bed-box, further system members like blood sampling ports, etc. can be mounted. Preferably, the other open end of the water column 110 end into a clamping piece on the monitor cable 108 between the electrical circuits and can be fixed at a suitable location at the height of the heart. Further, additional clamping pieces can be provided on the monitor cable 108 to allow fasten a rinsing conduit.

To the luer access 124 of the housing 95 a capillary valve or a flow control unit, for instance according to FIGS. 3a to f, with a rinsing conduit or capillary can be connected. Thus, a continuous rinsing of catheter 1 is achieved and at the same time a decoupling of the rinsing conduit that is tampering with the accuracy of the measuring signals and the blood sample units from the pressure channel is achieved.

What is claimed is:

1. A blood vessel catheter system, comprising:
   a catheter tube having a first portion configured for insertion into a blood vessel of a patient, and a second portion configured to remain outside the body of the patient when the first end is inside the blood vessel;
   a pressure sensor configured for connection outside of the patient's body to the second portion of the catheter tube, wherein the pressure sensor is configured to sense pressure in a liquid inside the catheter tube as an indication of a blood pressure of the patient, wherein the pressure sensor is configured to generate an electric pressure signal indicative of the blood pressure, and wherein the pressure sensor includes an electric interface configured to releasably couple the pressure sensor to a reusable measurement unit;
   a reservoir of rinsing fluid connected to the second portion of the catheter tube;
   a stop cock connected to the second portion of the catheter tube and configured for selective placement into at least:
      a rinsing position in which the stop cock allows a flow of rinsing fluid from the reservoir to the second portion of the catheter tube;
      a nulling position in which the stop cock establishes the application of a predetermined reference pressure to the pressure sensor, and
      a sampling position in which the stop cock prevents the flow of rinsing fluid from the reservoir to the second portion of the catheter tube; and
   a flow control unit positioned between the reservoir and the second portion of the catheter tube, said flow control unit comprising:
      an upstream end in fluid communication with the reservoir;

a downstream end in fluid communication the second portion of the catheter tube; and structure between the upstream end and the downstream end of the flow control unit defining first, second, and third fluid flow paths between the reservoir and the second portion of the catheter tube:

wherein said first fluid flow path includes a non-closing rinsing capillary configured to permanently allow fluid communication between the upstream end and the downstream end of the flow control unit, and a controlled flow of fluid between the reservoir and the second portion of the catheter tube when the stop cock is in its rinsing position;

wherein said second fluid flow path includes a first check valve configured to open when fluid pressure at the downstream end of the flow control unit exceeds a fluid pressure at the upstream end of the flow control unit by a first predetermined threshold pressure difference; and wherein said third fluid flow path includes a second check valve configured to open when fluid pressure at the upstream end of the flow control unit exceeds fluid pressure at the downstream end of the flow control unit by a second predetermined threshold pressure difference.

2. The blood vessel catheter system of claim 1, wherein said second predetermined threshold pressure difference is greater than said first predetermined threshold pressure difference.

* * * * *